US009810558B2

(12) United States Patent
Bates et al.

(10) Patent No.: US 9,810,558 B2
(45) Date of Patent: Nov. 7, 2017

(54) PRESSURE-BASED AIRFLOW SENSING IN PARTICLE IMPACTOR SYSTEMS

(71) Applicant: Particle Measuring Systems, Inc, Boulder, CO (US)

(72) Inventors: Thomas Bates, Westminster, CO (US); Cliff Ketcham, Golden, CO (US); Paul B. Hartigan, Longmont, CO (US); Ronald W. Adkins, Erie, CO (US)

(73) Assignee: PARTICLE MEASURING SYSTEMS, INC., Boulder, CO (US)

( * ) Notice: Subject to any disclaimer, the term of this patent is extended or adjusted under 35 U.S.C. 154(b) by 0 days.

(21) Appl. No.: 14/656,170

(22) Filed: Mar. 12, 2015

(65) Prior Publication Data
US 2015/0355000 A1 Dec. 10, 2015

Related U.S. Application Data

(60) Provisional application No. 61/953,252, filed on Mar. 14, 2014.

(51) Int. Cl.
*G01N 15/02* (2006.01)
*G01N 1/22* (2006.01)
(Continued)

(52) U.S. Cl.
CPC ............... *G01F 1/34* (2013.01); *G01F 1/28* (2013.01); *G01F 1/36* (2013.01); *G01F 1/42* (2013.01); *G01F 1/74* (2013.01); *G01F 1/76* (2013.01)

(58) Field of Classification Search
None
See application file for complete search history.

(56) References Cited

U.S. PATENT DOCUMENTS 4,571,079 A 2/1986 Knollenberg
4,594,715 A 6/1986 Knollenberg
(Continued)

FOREIGN PATENT DOCUMENTS

CA 1136882 12/1982
EP 0 015 170 9/1980

OTHER PUBLICATIONS

Biswas et al. (1984) "High-velocity inertial impactors," *Environ. Sci. Technol.* 18(8):611-616.
(Continued)

*Primary Examiner* — Harshad R Patel
(74) *Attorney, Agent, or Firm* — Lathrop Gage LLP

(57) ABSTRACT

Provided are systems and methods for accurate sensing of particle concentrations in fluids by employing a particle impactor system that allows for collection, growth and analysis of biological particles. The disclosed systems and methods make use of a pressure based flow sensor which permits the particle impactor system systems to accurately and reliably provide measurements of biological particle concentrations in the ambient environment. By incorporation of pressure sensors and pressure measurements into the flow measurement techniques, embodiments provide for the ability to use a particle impactor system to accurately measure environmental biological particle concentrations at a variety of atmospheric pressure conditions, such as at high altitude or with minimal perturbation from atmospheric weather conditions, without requiring recalibration or other adjustment of the sensors and control systems.

39 Claims, 6 Drawing Sheets

(51) Int. Cl.
  *G01F 1/34* (2006.01)
  *G01F 1/28* (2006.01)
  *G01F 1/76* (2006.01)
  *G01F 1/36* (2006.01)
  *G01F 1/42* (2006.01)
  *G01F 1/74* (2006.01)

(56) References Cited

U.S. PATENT DOCUMENTS

| | | |
|---|---|---|
| 4,665,529 A | 5/1987 | Baer et al. |
| 4,685,802 A | 8/1987 | Saito et al. |
| 4,723,257 A | 2/1988 | Baer et al. |
| 4,753,530 A | 6/1988 | Knight et al. |
| 4,798,465 A | 1/1989 | Knollenberg |
| 4,893,928 A | 1/1990 | Knollenberg |
| 4,896,048 A | 1/1990 | Borden |
| 4,984,889 A | 1/1991 | Sommer |
| 5,032,721 A | 7/1991 | Bacon et al. |
| 5,092,675 A | 3/1992 | Sommer |
| 5,095,206 A | 3/1992 | Bacon, Jr. et al. |
| 5,234,838 A | 8/1993 | Bacon, Jr. |
| 5,282,151 A | 1/1994 | Knollenberg |
| 5,283,199 A | 2/1994 | Bacon, Jr. et al. |
| RE34,729 E | 9/1994 | Sipes, Jr. |
| 5,467,188 A | 11/1995 | Miyashita |
| 5,467,189 A | 11/1995 | Kreikebaum et al. |
| 5,515,164 A | 5/1996 | Kreikebaum et al. |
| 5,600,438 A | 2/1997 | Kreikebaum et al. |
| 5,671,046 A | 9/1997 | Knowlton |
| 5,726,753 A | 3/1998 | Sandberg |
| 5,751,422 A | 5/1998 | Mitchell |
| 5,805,281 A | 9/1998 | Knowlton et al. |
| 5,825,487 A | 10/1998 | Felbinger et al. |
| 5,861,950 A | 1/1999 | Knowlton |
| 5,889,589 A | 3/1999 | Sandberg |
| 5,903,338 A | 5/1999 | Mavliev et al. |
| 5,922,976 A * | 7/1999 | Russell ................ G01N 15/02 73/865.5 |
| 6,167,107 A | 12/2000 | Bates |
| 6,246,474 B1 | 6/2001 | Cerni et al. |
| 6,275,290 B1 | 8/2001 | Cerni et al. |
| 6,615,679 B1 | 9/2003 | Knollenberg et al. |
| 6,709,311 B2 | 3/2004 | Cerni |
| 6,854,460 B1 * | 2/2005 | Shofner, II ........ A61M 15/0065 128/203.12 |
| 6,859,277 B2 | 2/2005 | Wagner et al. |
| 6,903,818 B2 | 6/2005 | Cerni et al. |
| 6,945,090 B2 | 9/2005 | Rodier |
| 7,030,980 B1 | 4/2006 | Sehler et al. |
| 7,088,446 B2 | 8/2006 | Cerni |
| 7,088,447 B1 | 8/2006 | Bates et al. |
| 7,208,123 B2 | 4/2007 | Knollenberg et al. |
| 7,235,214 B2 | 6/2007 | Rodier et al. |
| RE39,783 E | 8/2007 | Cerni et al. |
| 7,456,960 B2 | 11/2008 | Cerni et al. |
| 7,576,857 B2 | 8/2009 | Wagner |
| 7,667,839 B2 | 2/2010 | Bates |
| 7,796,255 B2 | 9/2010 | Miller |
| 7,916,293 B2 | 3/2011 | Mitchell et al. |
| 7,973,929 B2 | 7/2011 | Bates |
| 7,985,949 B2 | 7/2011 | Rodier |
| 8,027,035 B2 | 9/2011 | Mitchell et al. |
| 8,154,724 B2 | 4/2012 | Mitchell et al. |
| 8,174,697 B2 | 5/2012 | Mitchell et al. |
| 8,427,642 B2 | 4/2013 | Mitchell et al. |
| 8,800,383 B2 | 8/2014 | Bates |
| 2002/0033173 A1 * | 3/2002 | Shofner, II ........ A61M 15/0065 128/200.22 |
| 2003/0221996 A1 * | 12/2003 | Svoronos ............ B01D 46/2403 209/1 |
| 2005/0028593 A1 | 2/2005 | Rodier |
| 2007/0289390 A1 | 12/2007 | Ascheman |
| 2009/0078862 A1 | 3/2009 | Rodier et al. |
| 2009/0190128 A1 | 7/2009 | Cerni et al. |
| 2009/0268202 A1 | 10/2009 | Wagner |
| 2014/0261824 A1 * | 9/2014 | Byers ..................... B24B 57/02 137/896 |
| 2015/0075301 A1 * | 3/2015 | Scialo ................ G01N 1/2208 73/863.22 |
| 2015/0259723 A1 * | 9/2015 | Hartigan .................. C12Q 1/24 435/5 |
| 2015/0260617 A1 * | 9/2015 | Ketcham .............. G01N 1/2208 73/863.22 |

OTHER PUBLICATIONS

Knollenberg (1985) "Measurement of Particle Sizes Below 0.1 Micrometers," Journal of Environmental Science.
International Search Report and Written Opinion for corresponding international application PCT/US15/20181, dated Jun. 24, 2015, 10 pages.

* cited by examiner

PRESSURE-BASED AIRFLOW SENSING IN PARTICLE IMPACTOR SYSTEMS

CROSS-REFERENCE TO RELATED APPLICATIONS

This application claims the benefit of and priority to U.S. Provisional Application No. 61/953,252, filed on Mar. 14, 2014, which is hereby incorporated by reference in its entireties to the extent not inconsistent herewith.

BACKGROUND

The invention is in the field of particle sampling, collection and analysis. The invention relates generally to devices and methods for sampling and characterizing particles in fluids including air and process chemicals (e.g., gases and liquids) for applications including the evaluation of contaminants in a range of cleanroom and manufacturing environments, and, more particularly, to airflow systems that provide precise volumetric airflow measurements to particle sampling systems.

Cleanrooms and clean zones are commonly used in semiconductor and pharmaceutical manufacturing facilities. For the semiconductor industry, an increase in airborne particulate concentration can result in a decrease in fabrication efficiency, as particles that settle on semiconductor wafers will impact or interfere with the small length scale manufacturing processes. For the pharmaceutical industry, where this type of real-time efficiency feedback is lacking, contamination by airborne particulates and biological contaminants puts pharmaceutical products at risk for failing to meet cleanliness level standards established by the Food and Drug Administration (FDA).

Standards for the classification of cleanroom particle levels and standards for testing and monitoring to ensure compliance are provided by ISO 14664-1 and 14664-2. Aerosol optical particle counters are commonly used to determine the airborne particle contamination levels in cleanrooms and clean zones and liquid particle counters are used to optically measure particle contamination levels in process fluids. Where microbiological particles are a particular concern, such as in the pharmaceutical industry, not only is quantification of the number of airborne particles important, but evaluating the viability and identity of microbiological particles is also important. ISO 14698-1 and 14698-2 provide standards for evaluation of cleanroom and clean zone environments for biocontaminants.

Collection and analysis of airborne biological particles is commonly achieved using a variety of techniques including settling plates, contact plates, surface swabbing, fingertip sampling and impactor-based active air samplers. Cascade impactors have traditionally been used for collection and sizing of particles. In these devices, a series of accelerations and inertial impacts successively strip smaller and smaller particles from a fluid flow. Each single stage of an inertial impactor operates on the principle that particles suspended in air can be collected by forcing a dramatic change in the direction of the particle containing airflow, where the inertia of the particle will separate the particle from the airflow streamlines and allow it to impact on the surface. Biswas et al. describe the efficiency at which particles can be collected in a high velocity inertial impactor (*Environ. Sci. Technol.*, 1984, 18(8), 611-616).

In many cleanroom environments, retrieving size information from a particle impactor is not necessary. In this case, a single stage active air sampling impactor system is sufficient to collect biological particle concentrations subject to subsequent detection and analysis. In an impactor-based active air sampler used for collection of biological particles, the impact/collection surface commonly comprises a growth medium, such as an agar plate, as would be used with other biological particle collection techniques. After the particles are collected onto the growth media surface, the media is incubated to allow the biological particles to reproduce. Once the colonies reach a large enough size, they can be identified and characterized, for example using microscopic imaging, fluorescence, staining or other techniques, or simply counted visually by eye or by image analysis techniques.

For these types of biological particle collection and analysis techniques, various operational aspects are important to ensure efficient collection, detection and analysis. For example, the collection efficiency may be of high importance, as failing to detect that biological particles are present in cleanroom air can result in the cleanroom environment having higher levels of contamination than detected. Upon determination that under counting has occurred, pharmaceutical products made in those environments can be identified as failing to meet required standards, potentially leading to costly product recalls. Similarly, failing to ensure that the viability of collected biological particles is maintained during the collection process will also result in under counting. Such a situation can arise, for example, if the collected biological particles are destroyed, damaged or otherwise rendered non-viable upon impact with the growth medium, such that the collected particles do not replicate during the incubation process and, therefore, cannot be subsequently identified.

On the opposite extreme, biological particle concentrations can be overestimated due to false positives. Over counting of this nature arises where a biological particle that is not collected from the cleanroom air, but is otherwise placed in contact with the growth medium, is allowed to replicate during the incubation process and is improperly identified as originating from the cleanroom air. Situations that contribute to false positives include failing to properly sterilize the growth medium and collection system prior to particle collection and improper handling of the growth medium by cleanroom personnel as it is installed into a particle collection system and/or removed from the particle collection system and placed into the incubator. Again, this can result in a pharmaceutical product being identified as failing to meet required standards. Without sufficient measures to identify false positives, such a situation can result in pharmaceutical products that actually meet the required standards, but are destroyed due to an overestimation of biological particle concentration in the cleanroom air indicating that the standards were not met.

There remains a need in the art for particle collection systems capable of achieving efficient sampling of biological particles. For example, particle collection systems are needed for cleanroom and manufacturing applications that provide high particle collection efficiencies while maintaining the viabilities of collected bioparticles. In addition, particle collection systems are needed for cleanroom and manufacturing applications that reduce the occurrence of false positive detection events.

It is desirable in the field of particle collection systems to determine the number of particles for an exact volumetric flow rate (i.e., one cubic foot per minute, or "CFM") as sampled from the ambient environment within the cleanroom or clean zone. By way of example, particle collection systems in cleanrooms typically assume that contamination levels are measured relative to a volume of air, and not relative to mass, since the mass of a given volume of air can vary by over 20% due to elevational changes alone. Weather fronts induce additional mass-per-volume differentials of up to 3%.

Therefore, one problem in conventional particle collection systems is that actual volumetric flow rate is calibrated for a given pressure, typically at "sea level," such that particle counting at other locales does not reflect a correct volumetric flow rate. Manual adjustments can be made to compensate for these errors, except that continuous manual adjustment is needed to ensure accuracy over changing environmental (e.g., elevation and barometric pressure) conditions.

SUMMARY

The following patents provide useful background information for the invention and relating to particle sensors and airflow systems: U.S. Pat. Nos. 6,167,107; 5,825,487; 5,600,438; 5,515,164; 5,467,189; 4,984,889; 4,594,715; and 4,571,079. Each of the aforementioned patents is incorporated herein by reference.

Systems and methods of the invention provide for accurate sensing of particle concentrations in fluids, such as air, by employing a particle impactor system that provides for collection, growth and/or analysis of biological particles. The systems and methods of the invention make use of a pressure based flow sensor which permits the particle impactor systems to accurately and reliably provide measurements of biological particle concentrations in the ambient environment, for example, providing accurate particle concentrations corresponding to a well-defined volume of gas sampled. By incorporation of pressure sensors and pressure measurements into the flow measurement techniques, embodiments of the invention provide for the ability to use a particle impactor system to accurately measure environmental biological particle concentrations at a variety of atmospheric pressure conditions, such as at high altitude or with minimal perturbation from atmospheric weather conditions, without requiring recalibration or other adjustment of the sensors and control systems.

In a first aspect, the present invention provides methods of controlling and measuring a volumetric flow rate of a fluid flow through a particle impactor. In an embodiment, an exemplary method of this aspect for controlling a volumetric flow rate comprises the steps of: pulling or otherwise flowing a fluid through a plurality of intake apertures of a sampling head of a particle impactor; determining a flow rate of the fluid; determining ambient pressure; determining the volumetric flow rate as a function of the flow rate of the fluid and the ambient pressure; and controlling the particle impactor using the volumetric flow rate; for example, wherein controlling includes selective adjustment of fluid flow conditions through the system. In an embodiment, an exemplary method of this aspect for measuring a volumetric flow rate comprises the steps of: pulling the fluid through a plurality of intake apertures of a sampling head of the particle impactor; determining a flow rate of the fluid; determining ambient pressure; and determining the volumetric flow rate as a function of the flow rate of the fluid and the ambient pressure. In a specific embodiment, the ambient pressure is atmospheric pressure, such as the pressure of the environment surrounding the particle impactor. In an embodiment, the method uses only two pressure sensors. Optionally, the fluid comprises air or one or more process gases. In exemplary embodiments, the fluid contains particles.

In certain embodiments, the particle impactor comprises: a sampling head having the plurality of intake apertures; an impact surface positioned in fluid communication with the sampling head; and an impactor base supporting the impact surface, wherein the impactor base comprises a fluid outlet. In embodiments, for example, the sampling head and the impactor base together form a fluid tight seal such that the fluid can only flow into or out of the particle impactor through the plurality of intake apertures and the fluid outlet. The systems further comprises one or more pressure sensors, such as absolute and/or differential pressure sensors, positioned to measure a pressure of the fluid within the particle impactor, the ambient pressure or both a pressure of the fluid within the particle impactor and the ambient pressure. In an embodiment, the impactor base is in fluid communication with one or more pressure sensors positioned to measure one or more of a pressure of the fluid within the particle impactor system, differential pressure of the fluid within the particle impactor system and the ambient pressure.

In an embodiment, for example, the particle impactor further comprises a restriction along a flow path of the fluid flow within the particle impactor system. In an embodiment, for example, the particle impactor system further comprises a first pressure sensor comprising a differential pressure sensor positioned to measure a differential pressure across the restriction. In an embodiment, for example, the differential pressure sensor measures a ratio or a difference of a first pressure upstream of the restriction and a second pressure downstream of the restriction. In an embodiment, for example, the differential pressure sensor comprises a differential pressure sensor that directly measures the ratio or difference between a pressure upstream of the restriction and a pressure downstream of the restriction. In an embodiment, for example, the differential pressure sensor comprises a first absolute pressure sensor positioned to measure a pressure upstream of the restriction and a second absolute pressure sensor positioned to pressure downstream of the restriction, thereby providing a measurement of differential pressure.

In an embodiment, the particle impactor system further comprises a second pressure sensor for measuring the ambient pressure inside or outside the system. In an embodiment, the particle impactor system further comprises a third pressure sensor, wherein the second pressure sensor measures a ambient pressure outside of the system and the third pressure sensor measures an pressure inside the system. In an embodiment, the particle impactor system further comprises a mass flow sensor for determining the flow rate of the fluid, wherein the mass flow sensor is positioned in fluid communication with the plurality of intake apertures, the fluid outlet or both the plurality of intake apertures and the fluid outlet. In an embodiment, the step of determining the ambient pressure comprises determining an absolute pressure outside the particle impactor system, determining an absolute pressure within the particle impactor system, or determining both an absolute pressure outside the particle impactor system an absolute pressure within the particle impactor system.

In embodiments, measurement of one or more absolute pressure values is useful, for example, for correcting for a change in or otherwise taking into account a density of a fluid in determination of a volumetric flow rate. In certain embodiments, however, differential pressure measurements provide information useful for determining a change in density as fluid is compressed or expanded. In one embodiment, the step of determining the ambient pressure comprises determining an absolute pressure within the particle impactor and determining an absolute pressure outside the particle impactor. In an embodiment, for example, a method of this aspect further comprises a step of measuring a differential pressure between a pressure within the particle impactor and the ambient pressure. In an exemplary embodiment the step of determining the flow rate of the fluid comprises determining a mass flow rate of the fluid.

In a specific embodiment, methods of this aspect utilize ratios, differences and/or products of measured pressure or pressure differentials to determine or estimate a volumetric flow rate through the system. In an exemplary embodiment, the step of determining the volumetric flow rate comprises determining the volumetric flow rate as Q in the following relationship (FX1):

$$Q = k \cdot [(2 \cdot P_{DPS})/P_{APSE}]^{1/2} \quad (FX1);$$

where k is an empirically determined constant, $P_{DPS}$ is a differential pressure within the system and $P_{APSE}$ is the ambient pressure. Use of formula (FX1) for determination of volumetric flow rate is particularly useful for methods using only two pressure sensors; e.g. a differential pressure sensor and an absolute pressure sensor. In an embodiment, the step of determining the volumetric flow rate comprises determining the volumetric flow rate as Q in the following relationship (FX2):

$$Q = k \cdot [(P_{APSO} \cdot P_{DPS})]^{1/2}/P_{APSE} \quad (FX2);$$

where k is an empirically determined constant, PAPSO is an absolute pressure within the particle impactor system, $P_{DPS}$ is a differential pressure and $P_{APSE}$ is the ambient pressure. Use of formula (FX2) for determination of volumetric flow rate is particularly useful for methods using three pressure sensors. As will be understood by one having skill in the art in connection with equations (FX1) and (FX2), $P_{DPS}$ is a differential pressure within the system, for example, a differential pressure across a restriction. As will be understood by one having skill in the art in connection with equations (FX1) and (FX2), $P_{APSE}$ is an ambient pressure, such as the atmospheric pressure of the environment surrounding the system. As will be understood by one having skill in the art in connection with equations (FX1) and (FX2), $P_{APSO}$ is an absolute pressure within the particle impactor system, such as an absolute pressure upstream of a restriction within the system.

In an embodiment, for example, the step of determining the volumetric flow rate comprises utilizing the following relationship (FX3) in evaluation of Q:

$$Q = k \cdot [(2\Delta P)/\rho]^{1/2} \quad (FX3);$$

wherein k is an empirically determined constant, $\Delta P$ is a differential pressure across a restriction in the particle impactor and $\rho$ is a density of the fluid. In a specific embodiment, the step of determining the flow rate of the fluid comprises determining a differential pressure across a restriction within the particle impactor.

As will be generally understood by one having skill in the art, values of k in equations (FX1), (FX2) and (FX3) can be independently determined using a variety of methods including via calibration techniques. In some embodiments, for example, k is a linear scale factor applied at the time of the flow system calibration.

In certain embodiments, methods of this aspect include controlling the volumetric flow rate, such as to maintain the volumetric flow rate through a particle impactor system at a specified value or within a specified range (e.g., within at least 10%, or for some applications within at least 5% or for some applications within at least 1% of a specified value). In an exemplary embodiment, a method of this aspect further comprises a step of: increasing an absolute pressure within the particle impactor system if the volumetric flow rate is determined to be larger than a specified value; or reducing an absolute pressure within the particle impactor system if the volumetric flow rate is determined to be smaller than a specified value. Optionally, the fluid flow is generated by one or more flow generating devices selected from the group consisting of a fan, a blower, a pump and any combination of these. In an exemplary embodiment, a method of this aspect comprises a step of: reducing a speed or flow rate of one or more of the flow generating devices if the volumetric flow rate is determined to be larger than a first specified value; or increasing a speed or flow rate of one or more of the flow generating devices if the volumetric flow rate is determined to be smaller than a second specified value. In an embodiment, for example, the specified value is selected over the range of 0.01 CFM to 20 CFM, and optionally for some applications 0.05 CFM to 10 CFM.

In another aspect, the present invention provides particle impactor systems. Particle impactor systems of the invention are useful for accurately collecting and measuring particle concentrations in a fluid, such as biological particle concentrations in cleanroom air. As with the above described methods, particle impactors of the invention optionally include components and/or sensors for taking pressure and/or pressure changes into consideration when determining a volumetric flow rate through the system. In certain embodiments, having accurate volumetric flow measurements is important for determining particle concentrations, for example, for ensuring compliance with regulatory requirements.

In a specific embodiment, a particle impactor comprises: (i) a sampling head having a plurality of intake apertures; (ii) an impact surface positioned in fluid communication with the sampling head; (iii) an impactor base supporting the impact surface, wherein the impactor base comprises a fluid outlet; (iv) a flow restriction positioned in fluid communication with the plurality of intake apertures, the fluid outlet or both the plurality of intake apertures and the fluid outlet; (v) first pressure sensor comprising a differential pressure sensor positioned to measure a differential pressure across the restriction; and (vi) a second pressure sensor positioned to measure an ambient pressure inside or outside of the system. In an embodiment, the system comprises only two pressure sensors, such as a differential pressure sensor positioned to measure a pressure differential across a restriction within the system and an absolute pressure sensor positioned to measure absolute pressure corresponding to ambient pressure.

In an embodiment, for example, the first pressure sensor comprises a differential pressure sensor capable of directly measuring the differential pressure. In an embodiment, for example, the differential pressure sensor comprises a first absolute pressure sensor positioned to measure a pressure upstream of the restriction and a second absolute pressure sensor positioned to pressure downstream of the restriction. In an embodiment, for example, the particle impactor system further comprises a third pressure sensor, wherein the second pressure sensor measures an ambient pressure outside of the system and the third pressure sensor measures an ambient pressure inside the system. In an embodiment, the system further comprises a mass flow sensor positioned in fluid communication with the plurality of intake apertures, the fluid outlet or both the plurality of intake apertures and the fluid outlet.

Optionally, a particle impactor further comprises one or more flow generating devices selected from the group consisting of a fan, a blower, a pump and any combination of these, wherein the one or more flow generating device are positioned in fluid communication with the plurality of intake apertures, the fluid outlet or both the plurality of intake apertures and the fluid outlet. In an exemplary particle impactor embodiment, the sampling head and the impactor base together form a fluid tight seal such that fluid can only, or substantially only, flow into or out of the particle impactor through the plurality of intake apertures and the fluid outlet (e.g., at least 95% of the fluid flow flows into or out of the particle impactor through the plurality of intake apertures and the fluid outlet). In one embodiment, an o-ring is provided between the sampling head and the impactor base to form the fluid tight seal.

In exemplary embodiments, particle impactor systems of the invention incorporate a processor or other control system for determining, monitoring and/or controlling a flow rate through the system and/or for controlling other operational aspects of the system. In a specific embodiment, a particle impactor further comprises a processor positioned in data communication with one or more pressure sensors and/or a mass flow sensor, with the processor programmed with instructions that when executed determine a volumetric flow rate using pressure measurements from the pressure sensors and/or mass flow rate measurements from the mass flow sensor. The processor of this aspect may be implemented by hardware or a combination of hardware and software.

In an embodiment, for example, the processor is programmed with instructions that when executed determine the volumetric flow rate as Q according to the following relationship (FX1):

$$Q=k\cdot[(2\cdot P_{DPS})/P_{APSE}]^{1/2} \qquad \text{(FX1)};$$

where k is an empirically determined constant, $P_{DPS}$ is a differential pressure within the system and $P_{APSE}$ is the ambient pressure. Use of formula (FX1) for determination of volumetric flow rate is particularly useful for systems using only two pressure sensors; e.g., a differential pressure sensor and absolute pressure sensor. In an embodiment, for example, the processor is programmed with instructions that when executed determine the volumetric flow rate as Q according to the following relationship (FX2):

$$Q=k\cdot[(P_{APSO}\cdot P_{DPS})]^{1/2}/P_{APSE} \qquad \text{(FX2)};$$

where k is an empirically determined constant, $P_{APSO}$ is an absolute pressure within the particle impactor, $P_{DPS}$ is a differential pressure and $P_{APSE}$ is the ambient pressure. Use of formula (FX2) for determination of volumetric flow rate is particularly useful for systems using three pressure sensors. As will be understood by one having skill in the art in connection with equations (FX1) and (FX2), $P_{APSE}$ is an ambient pressure, such as the atmospheric pressure of the environment surrounding the system. As will be understood by one having skill in the art in connection with equations (FX1) and (FX2), $P_{APSO}$ is an absolute pressure within the particle impactor system, such as an absolute pressure upstream of a restriction within the system.

Optionally, the processor is programmed with instructions that when executed determine the volumetric flow rate as Q according to the following relationship (FX3:

$$Q=k\cdot[(2\Delta P)/\rho]^{1/2} \qquad \text{(FX3)};$$

where ΔP is a differential pressure across the restriction in the system and ρ is a density of a fluid flowing through the restriction.

Optionally, a processor of a particle impactor system is positioned in data communication with a flow controller and is programmed with instructions that when executed adjust a flow set point of the flow controller. For example, in one embodiment, the flow controller is provided to control a fluid flow rate of one or more flow generating devices positioned in fluid communication with the plurality of intake apertures, the fluid outlet or both the plurality of intake apertures and the fluid outlet. In embodiments, the one or more flow generating devices are selected from the group consisting of a fan, a blower, a pump and any combination of these.

In one embodiment, for example, the particle impactor includes a plurality of pressure sensors and a blower or fan speed voltage controller. The controller optionally adjusts the speed of the blower or fan according to signals from the pressure sensors such that the flow is characterized by a preselected volumetric flow rate.

Embodiments of the impactors of the invention optionally include a high efficiency exhaust filter to filter air exhausted from the particle impactor, such as using a HEPA filter. Inclusion of such an exhaust filter is important in embodiments where the particle impactor is located in a cleanroom or clean zone and it is desired to prevent particles generated within the particle impactor, such as within or by a flow generation device, from exiting the system and contaminating the environment.

The invention is next described further in connection with preferred embodiments, and it will become apparent that various additions, subtractions, and modifications can be made by those skilled in the art without departing from the scope of the invention. Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

BRIEF DESCRIPTION OF THE DRAWINGS

A more complete understanding of the invention may be obtained by reference to the drawings, in which.

DETAILED DESCRIPTION

Figure 1A:
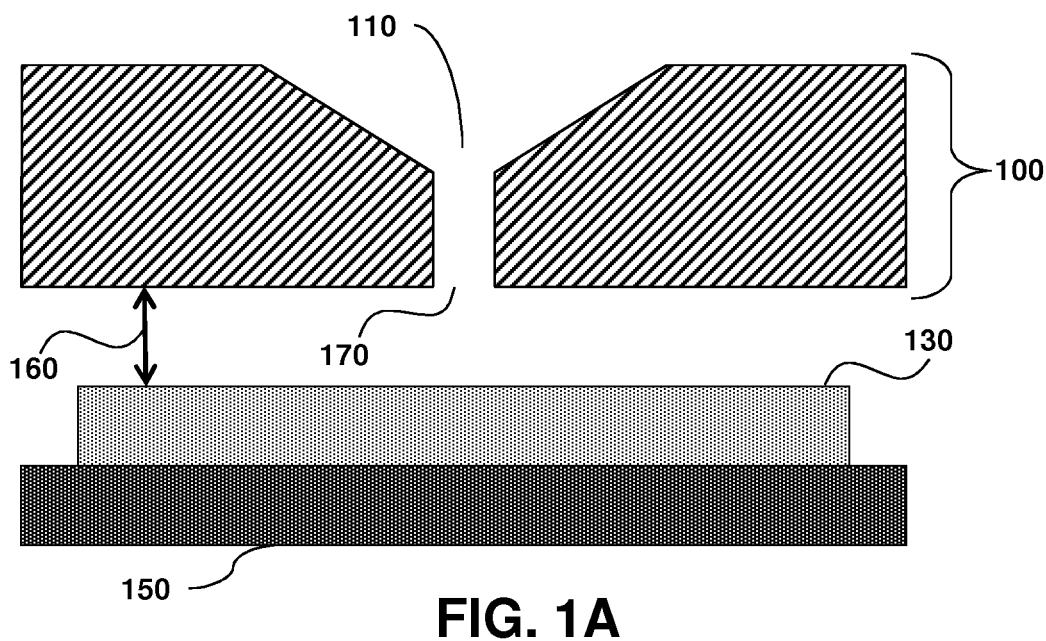
FIGS. 1A and 1B illustrate the construction and general principles of operation of a particle impactor, such as a particle impactor for the collection and analysis of biological particles.

In general the terms and phrases used herein have their art-recognized meaning, which can be found by reference to standard texts, journal references and contexts known to those skilled in the art. The following definitions are provided to clarify their specific use in the context of the invention.

"Particle" refers to a small object which is often regarded as a contaminant. A particle can be any material created by the act of friction, for example when two surfaces come into mechanical contact and there is mechanical movement. Particles can be composed of aggregates of material, such as dust, dirt, smoke, ash, water, soot, metal, minerals, or any combination of these or other materials or contaminants. "Particles" may also refer to biological particles, for example, viruses, spores and microorganisms including bacteria, fungi, archaea, protists, other single cell microorganisms and specifically those microorganisms having a size on the order of 1 to 20 μm. Biological particles include viable biological particles capable of reproduction, for example, upon incubation within a growth media. A particle may refer to any small object which absorbs or scatters light and is thus detectable by an optical particle counter. As used herein, "particle" is intended to be exclusive of the individual atoms or molecules of a carrier fluid, for example, such gases present in air (e.g., oxygen molecules, nitrogen molecules, argon molecule, etc) or process gases. Some embodiments of the present invention are capable of sampling, collecting, detecting, sizing, and/or counting particles comprising aggregates of material having a size greater than 50 nm, 100 nm, 1 μm or greater, or 10 μm or greater. Specific particles include particles having a size selected from 50 nm to 50 μm, a size selected from 100 nm to 10 μm, or a size selected from 500 nm to 5 μm.

The expression "sampling a particle" broadly refers to collection of particles in a fluid flow, for example, from an environment undergoing monitoring. Sampling in this context includes transfer of particles in a fluid flow to an impact surface, for example, the receiving surface of a growth medium. Sampling may refer to collection of particles having one or more preselected characteristics, such as size (e.g., cross sectional dimension such as diameter, effective diameter, etc.), particle type (biological or nonbiological, viable or nonviable, etc.) or particle composition. Sampling may optionally include analysis of collected particles, for example, via subsequent optical analysis, imaging analysis or visual analysis. Sampling may optionally include growth of viable biological particles, for sample, via an incubation process involving a growth medium. A sampler refers to a device for sampling particles.

Impactor refers to a device for sampling particles. In some embodiments, an impactor comprises a sampling head including one or more intake apertures for sampling a fluid flow containing particles, whereby at least a portion of the particles are directed on to an impact surface for collection, such as the receiving surface of a growth medium (e.g., culture medium such as agar, broth, etc.) or a substrate such as a filter. Impactors of some embodiments provide a change of direction of the flow after passage through the intake apertures, wherein particles having preselected characteristics (e.g., size greater than a threshold value) do not make the change in direction and, thus, are received by the impact surface. In some embodiments, for example, an impactor of the invention does not include a particle counter, such as an optical particle counter.

The expression "detecting a particle" broadly refers to sensing, identifying the presence of and/or characterizing a particle. In some embodiments, detecting a particle refers to counting particles. In some embodiments, detecting a particle refers to characterizing and/or measuring a physical characteristic of a particle, such as diameter, cross sectional dimension, shape, size, aerodynamic size, or any combination of these. A particle counter is a device for counting the number of particles in a fluid or volume of fluid, and optionally may also provide for characterization of the particles, for example, on the basis of size (e.g., cross sectional dimension such as diameter or effective diameter), particle type (e.g. biological or nonbiological, or particle composition. An optical particle counter is a device that detects particles by measuring scattering, emission or absorbance of light by particles.

"Flow direction" refers to an axis parallel to the direction the bulk of a fluid is moving when a fluid is flowing. For fluid flowing through a straight flow cell, the flow direction is parallel to the path the bulk of the fluid takes. For fluid flowing through a curved flow cell, the flow direction may be considered tangential to the path the bulk of the fluid takes.

"Optical communication" refers to an orientation of components such that the components are arranged in a manner that allows light or electromagnetic radiation to transfer between the components.

"Fluid communication" refers to the arrangement of two or more objects such that a fluid can be transported to, past, through or from one object to another. For example, in some embodiments two objects are in fluid communication with one another if a fluid flow path is provided directly between the two objects. In some embodiments, two objects are in fluid communication with one another if a fluid flow path is provided indirectly between the two objects, such as by including one or more other objects or flow paths between the two objects. For example, in one embodiment, the following components of a particle impactor are in fluid communication with one another: one or more intake apertures, an impact surface, a fluid outlet, a flow restriction, one or more pressure sensors, and/or a flow generating device. In one embodiment, two objects present in a body of fluid are not necessarily in fluid communication with one another unless fluid from the first object is drawn to, past and/or through the second object, such as along a flow path.

"Flow rate" refers to an amount of fluid flowing past a specified point or through a specified area, such as through intake apertures or a fluid outlet of a particle impactor. In one embodiment a flow rate refers to a mass flow rate, i.e., a mass of the fluid flowing past a specified point or through a specified area. In one embodiment a flow rate is a volumetric flow rate, i.e., a volume of the fluid flowing past a specified point or through a specified area.

"Pressure" refers to a measure of a force exhibited per unit area. In an embodiment, a pressure refers to a force exhibited by a gas or fluid per unit area. An "absolute pressure" refers to a measure of the pressure exerted by a gas or fluid per unit area as referenced against a perfect vacuum, near vacuum, a calibration pressure and/or a volume exerting zero force per unit area. Absolute pressure is distinguished from a "differential pressure" or "gauge pressure", which refers to a relative or difference in force exhibited per unit area in excess of or relative to a second pressure, such as an upstream pressure, a downstream pressure, an ambient pressure or atmospheric pressure.

Figure 1B:
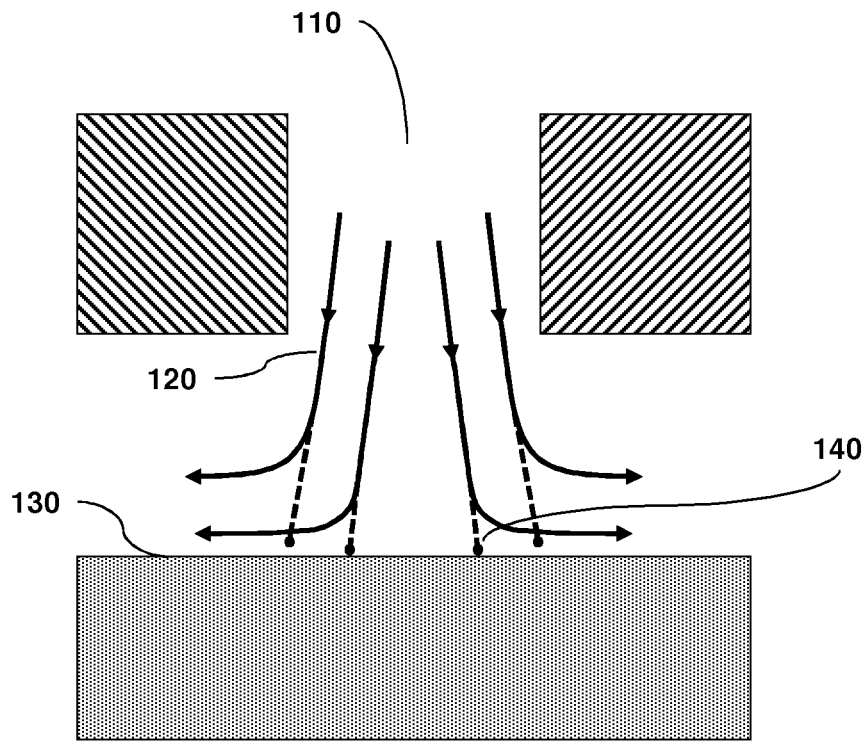
Figure 2A:
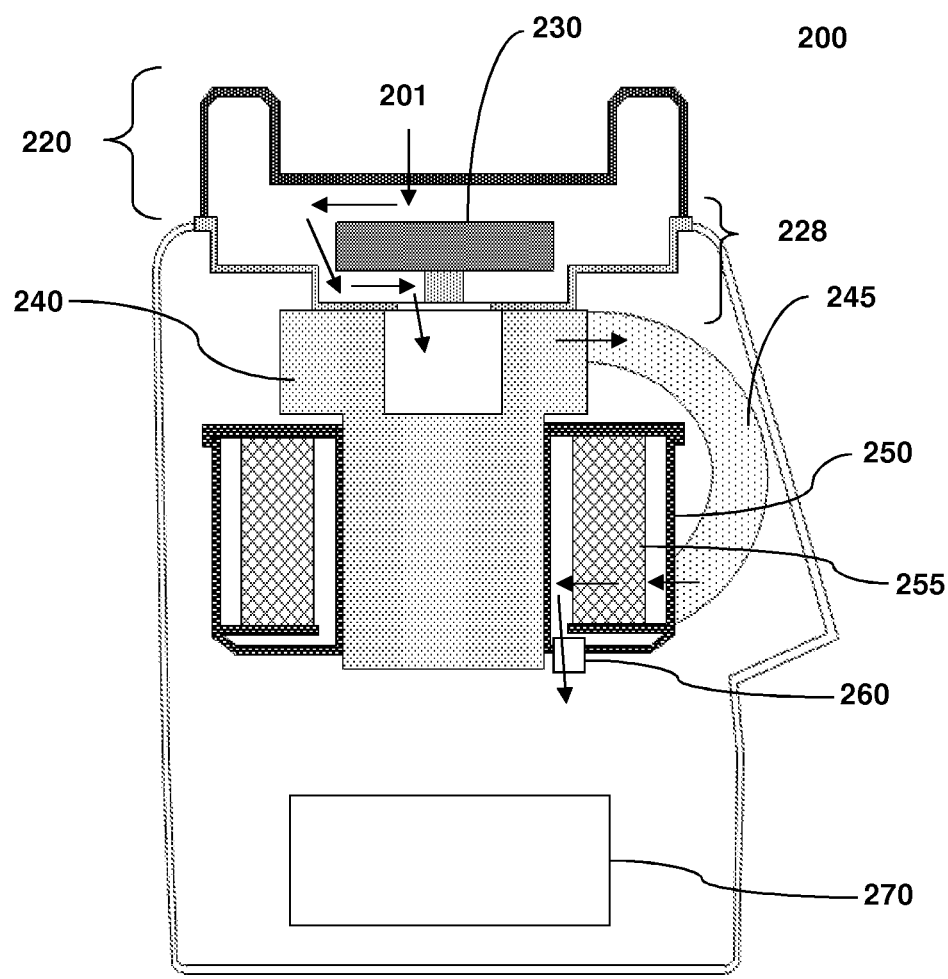
FIGS. 2A and 2B show a particle impactor system constructed according to the invention, including a particle impactor, fluid flow mechanics and sampling head.
Figure 2B:
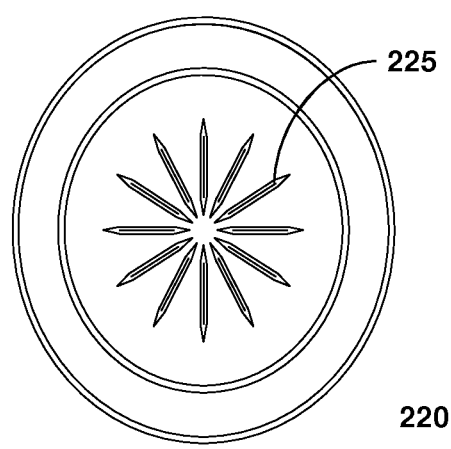

FIG. 1A provides a schematic diagram illustrating the general construction of a particle impactor and FIG. 1B illustrates an expanded view of a particle impactor to further illustrate the operational principal. As shown in these Figures, gas flow is directed through an intake aperture 110 in a sampling head 100 where it is accelerated towards an impact surface 130, which forces the gas to rapidly change direction, following flow paths or streamlines 120 under laminar, or near laminar, fluid flow conditions. Due to their momentum, particles 140 entrained in the gas flow are unable to make the rapid change in direction and impact on the impact surface 130. In the embodiment shown in FIGS. 1A and 1B, impact surface 130 is supported by impactor base 150. In embodiments, impact surface 130 comprises the receiving surface of a growth medium, such as agar, provided in a growth medium container or petri dish.

Viable biological particles collected on the impact surface, for example, can subsequently be incubated and grown and evaluated to provide an analysis of the composition of the fluid flow sampled. For collection of biological particles on impact surface 130, control of the separation distance 160, such as a separation distance between the exit 170 of the intake aperture 110 and the impact surface 130, is important. If the distance is too large, for example, the particles may sufficiently follow the fluid path so as to avoid impact with the impact surface. If the distance is too small, however, the particles may impact the impact surface with a force sufficient to render the particles non-viable or otherwise adversely affect the ability of a biological particle to sufficiently reproduce to be visually detected by a user.

FIG. 2A illustrates a cross-sectional diagram of particle impactor system 200 and FIG. 2B illustrates a top view of sampling head 220 of impactor system 200. Ambient fluid 201 is sampled by system 200 through a plurality of intake apertures 225 in sampling head 220, which sits atop impactor base 228. Sampling head 200 shown in FIG. 2B, includes 12 intake apertures 225 exemplified as slits arranged in a radial fashion, though other intake configurations are included in the scope of the invention, such as fewer, e.g., 1 intake aperture, or more, e.g., 20 intake apertures, or other intake configurations such as holes or inlet jets. Fluid is drawn past impact surface 230 and particles present in the fluid are collected on impact surface 230. In the embodiment shown in FIG. 2A, a blower 240 provides for the fluid flow into system 200 through intake apertures 225 and exhaust from blower 240 flows along flow path 245 to filter housing 250. The arrows in FIG. 2A schematically illustrate a flow path for fluid through system 200. The fluid is passed into filter housing 250 and through filter element 255 before passing back out of filter housing 250. As the fluid exits filter housing 250, it is passed through a flow sensor 260. Flow sensor 260 is optionally exemplified as a differential pressure sensor with a flow restriction. For example, differential sensor may be configured to directly measure differential pressure across the restriction or may be configured to measure the pressure differential using a first pressure sensor positioned on an upstream side of the flow restriction and second pressure sensor positioned on a downstream side of the flow restriction. In the embodiment shown in FIG. 2A, flow sensor 260 is provided downstream of filter element 255. Alternative, flow sensor 260 may be provided in other regions of the system including upstream of filter element 255 or connected to the outlet of the impactor base. Additional pressure sensors are optionally positioned outside of system 200 to measure the ambient pressure and/or pressure within the system.

System 200 optionally includes a control system 270 to control the fluid intake rate into system 200. Using flow sensor 260 and associated pressure sensors, a volumetric flow rate into the system can be determined. If such determined volumetric flow rate is smaller than a volumetric flow rate set point of the system, a signal is provided to blower 240 to increase the flow rate generated by blower 240, such as a signal to increase an impeller velocity of blower 240. Similarly, if such determined volumetric flow rate is larger than a volumetric flow rate set point of the system, a signal is provided to blower 240 to decrease the flow rate generated by blower 240, such as a signal to decrease an impeller velocity of blower 240.

FIG. 3A-3D illustrates various device configurations using pressure sensing within flow sensor 260 to attain accurate volumetric flow rates through system 200. FIG. 3A illustrates a device configuration using pressure sensing via a two pressure sensor configuration. As shown in this figure, the flow rate (molecules/second) of a gas sample such as air 301 in flow tube 346 is measured using differential pressure sensor 320 which measures the pressure differential across restricting orifice 360. To attain the number of particulates at a desired volumetric flow, volumetric flow is determined using the differential pressure and the ambient pressure as provided by flow sensor 320 and pressure sensor 324, respectively. In some embodiment, pressure sensor 324 is an absolute pressure sensor, position to determine ambient pressure outside or within system 200. Differential pressure flow sensor 320 is used in tandem with restricting orifice 360 to measure the differential pressure drop across orifice 360 caused by fluid flow through orifice 360. Absolute pressure sensor 324 is used to measure the absolute pressure of the ambient fluid 201. The control system of system 200 interprets the information provided by pressure sensors 320 and 324 and derives an output signal to control the speed of blower 240. System 200 thus provides a closed loop feedback control of blower 240. FIG. 3B illustrates an alternative device configuration using pressure sensing via a two pressure sensor configuration. As shown in the figure, differential pressure sensor 320 is provided to determine a pressure differential at a point upstream of restriction 360 relative to ambient pressure.

FIG. 3C illustrates a device configuration using pressure sensing via a three pressure sensor configuration. As shown in this figure, the flow rate (molecules/second) of a gas sample such as air 301 in flow tube 346 is measured using differential pressure sensor 320 positioned to determine the pressure differential across restricting orifice 360, pressure sensor 324 positioned to determine ambient pressure outside or within system 200 and pressure sensor 322 positioned to measure pressure within the system at a point upstream of the restriction. In some embodiments, for example, pressure drops in the upstream flow of pressure sensor 322 causes the fluid density at its location to be different than at the ambient environment. Therefore, the pressure ratio (pressure from pressure sensor 322 divided by pressure from pressure sensor 324) is, optionally, interpreted in order to maintain the required volumetric flow rate at differential pressure sensor 320, corresponding to a specific volumetric flow rate drawn from ambient environment. The control system of system 200 interprets the information provided by pressure sensors 320, 322, and 324 and derives an output signal to control the speed of blower 240. System 200 thus provides a closed loop feedback control of blower 240. FIG. 3D illustrates an alternative device configuration using pressure sensing via a three pressure sensor configuration. As shown in the figure, differential pressure sensor 320 is provided to determine a pressure differential at a point upstream of restriction 360 relative to ambient pressure.

System 200 provides an accurate volumetric flow rate as sampled from the ambient environment. System 200 is optionally intended to be used at elevations ranging approximately from sea level to 10,000 feet. In some embodiments, the differential pressure signal, $\Delta P$, generated by sensor 320 is proportional to the flow rate through flow sensor 260; however the Bernoulli equation requires that the fluid density at sensor 320 be known in order to derive the actual volumetric flow rate. Optionally, pressure sensor is be used 322 is used to measure this fluid density.

System 200 thus produces an accurate volumetric flow rate at the current ambient environment conditions as compensated for varying density, due to site elevation, and local air pressure changes, due to environmental conditions.

The following equations are useful in determining the volumetric flow rate:

$$\rho = PM/RT \quad \text{Ideal Gas Law:}$$

where $\rho$=Density (kg/m$^3$), P=Pressure (kPa), M=Molar mass of gas (28.97 kg/kmol for air), R=Universal Gas Constant (8.314 kJ/kmol-K) and T=Temperature (K).

$$Q = k \cdot [(2\Delta P)/\rho]^{1/2} \quad \text{Bernoulli equation:}$$

where Q=Volumetric Flow, k=empirically determined constant, $\Delta P$=Differential pressure and $\rho$=Density.

Figure 3A:
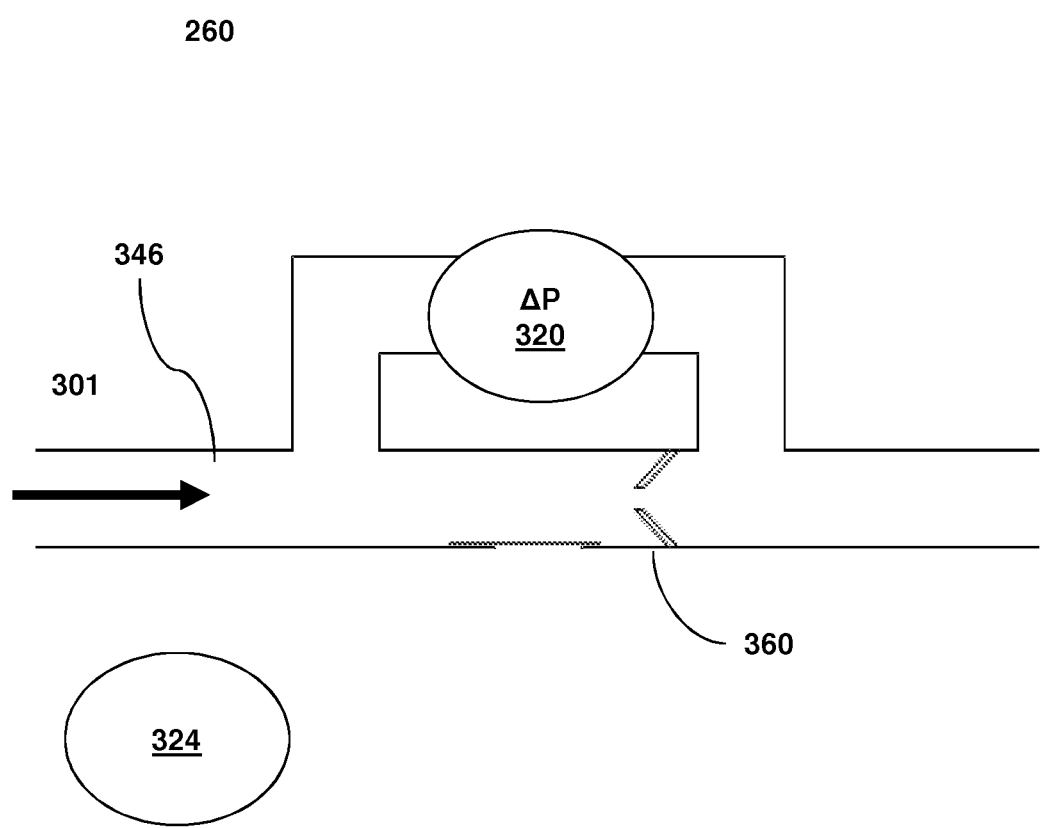
FIG. 3A-3D illustrates various device configurations using pressure sensing to attain accurate volumetric flow rates.
Figure 3B:
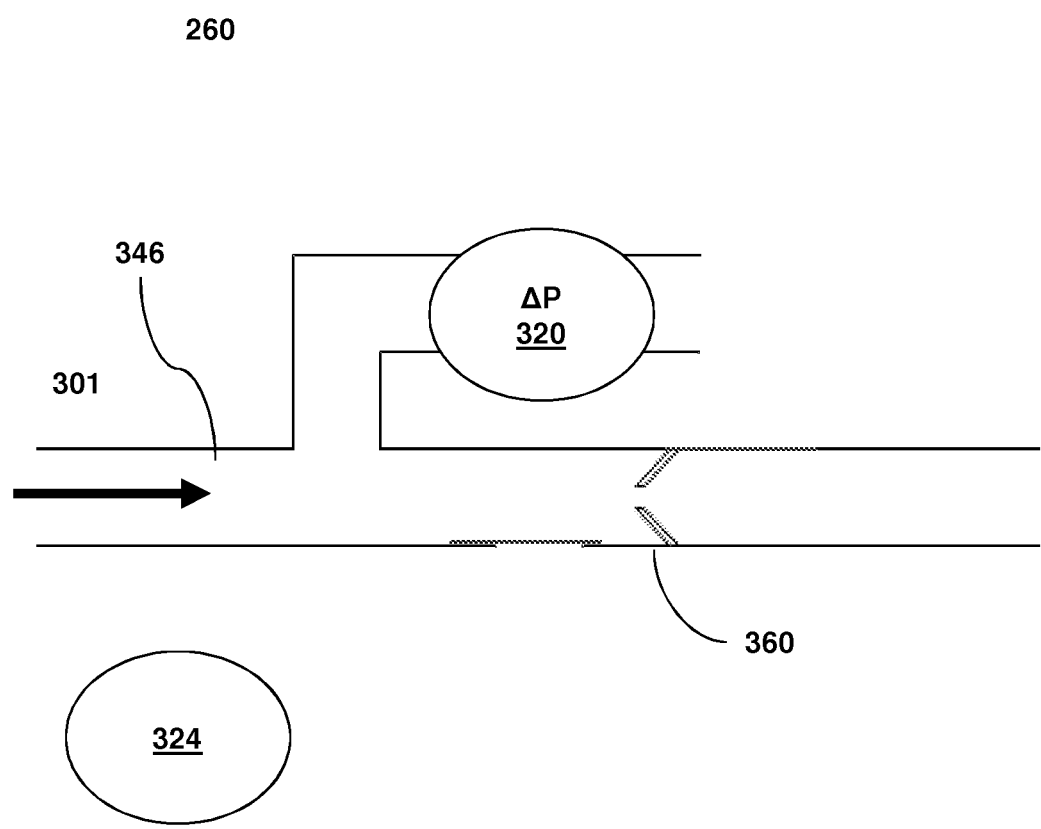

In the two pressure sensor configurations shown in FIGS. 3A and 3B, for example, a simplified equation (FX1) provides volumetric flow, Q, within sensor 260:

$$Q = k \cdot [(2 \cdot P_{DPS})/P_{APSE}]^{1/2} \quad (FX1);$$

where Q=Ambient Volumetric Flow, k=empirically determined constant, $P_{DPS}$=Differential pressure of airflow sensor 320, $P_{APSE}$=Pressure of pressure sensor 324.

Figure 3C:
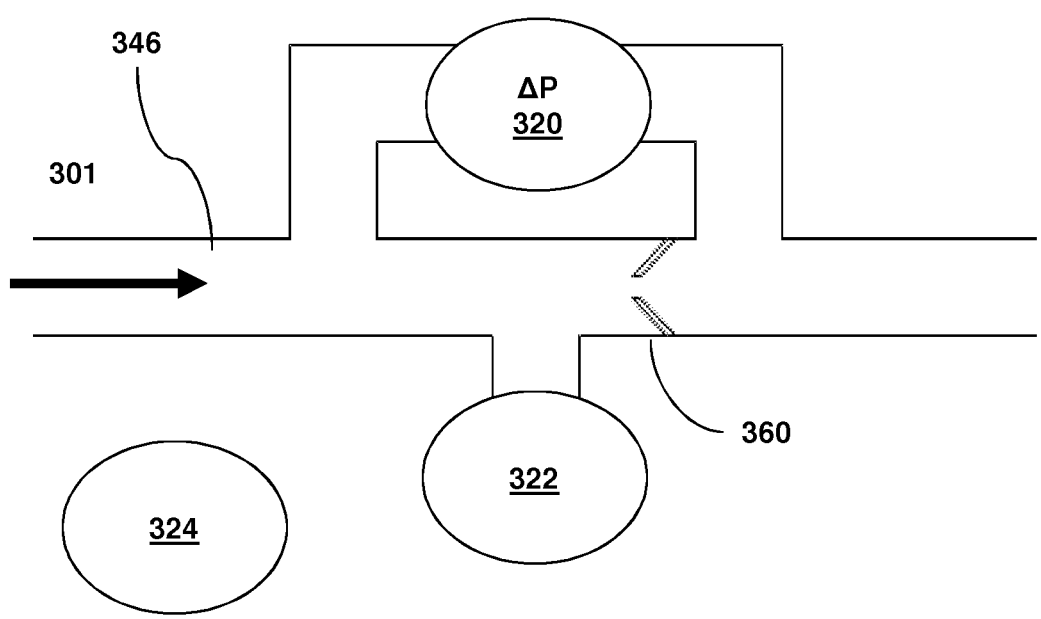
Figure 3D:
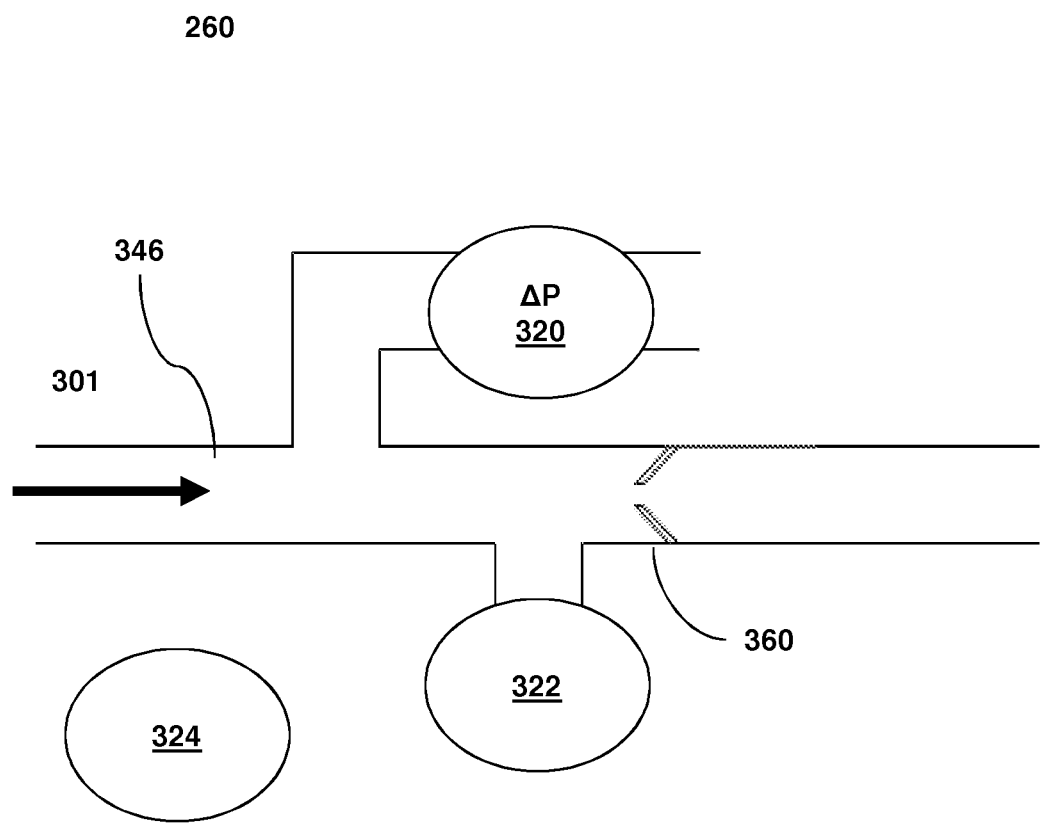

In the three pressure sensor configurations shown in FIGS. 3C and 3D, for example, a simplified equation (FX2) provides volumetric flow, Q, within sensor 260:

$$Q = k \cdot [(P_{APSO} \cdot P_{DPS})]^{1/2}/P_{APSE} \quad (FX2);$$

where k is an empirically determined constant, $P_{DPS}$=Differential pressure of airflow sensor 320, $P_{APSE}$=Pressure of pressure sensor 324 and $P_{APSO}$=Pressure of pressure sensor 322.

The invention thus attains objects including those apparent from the preceding description. Since certain changes may be made in the above methods and systems without departing from the scope of the invention, it is intended that all matter contained in the above description or shown in the accompanying drawing be interpreted as illustrative and not in a limiting sense. For example, those skilled in the art should appreciate that several radial or regenerative blowers can be used with the invention, such as the MINISPIRAL™ regenerative blowers (e.g., MDC part numbers SE12V21-037433 and SE12RE21-038700), and radial blower (part number 119349) by the Rotron Technical Motor Division of AMETEK®. Additionally, other flow generation devices, such as axial fans and pumps are optionally used to draw fluid through the intake apertures. Exemplary blowers include 114 mm Brushless Low-Voltage Blowers having model number 119349, 119494 and 119395 from AMETEK; Elmo Rietschle G-BH10, 2BH1 002 blowers of Gardner Denver Blower Division; and miniature radial blower C55H1 with internal driver, part numbers C55H1-12PS-04 and C55H1-24PS-04 by M.U.S. International. Optionally, a house vacuum line can be used to draw fluid through intake apertures in the systems and methods of the invention.

It is also to be understood that the following claims are to cover all generic and specific features of the invention described herein, and all statements of the scope of the invention which, as a matter of language, might be said to fall there between.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example "1, 2 and/or 3" is equivalent to "'1' or '2' or '3' or '1 and 2' or '1 and 3' or '2 and 3' or '1, 2 and 3'".

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method of controlling a volumetric flow rate of a fluid flow through a particle impactor system, the method comprising the steps of:
    pulling said fluid through a plurality of intake apertures of a sampling head of said particle impactor system, wherein said fluid contains a plurality of particles;
    pulling said fluid past an impact surface positioned in fluid communication with each of said plurality of intake apertures, causing a change in direction of said fluid, whereby at least a portion of the particles are directed onto said impact surface for collection;
    determining a flow rate of said fluid;
    determining ambient pressure;
    determining said volumetric flow rate as a function of said flow rate of said fluid and said ambient pressure; and
    controlling the fluid flow in said particle impactor system using said volumetric flow rate.

2. The method of claim 1, wherein said ambient pressure is atmospheric pressure.

3. The method of claim 1, wherein said particle impactor system comprises:
    said sampling head having said plurality of intake apertures; and
    an impactor base supporting said impact surface, wherein said impactor base comprises a fluid outlet;
    wherein said sampling head and said impactor base together form a fluid tight seal such that said fluid can only flow into or out of said particle impactor system through said plurality of intake apertures and said fluid outlet.

4. The method of claim 3, wherein said impactor base is in fluid communication with one or more pressure sensors positioned to measure one or more of a pressure of said fluid within said particle impactor system, a differential pressure of said fluid within said particle impactor system and said ambient pressure.

5. The method of claim 3, wherein said particle impactor system further comprises a restriction along a flow path of said fluid flow within said particle impactor system.

6. The method of claim 5, wherein said particle impactor system further comprises a first pressure sensor comprising a differential pressure sensor positioned to measure a differential pressure across said restriction.

7. The method of claim 6, wherein said differential pressure sensor measures a ratio or a difference of a first pressure upstream of said restriction and a second pressure downstream of said restriction.

8. The method of claim 6, wherein said differential pressure sensor comprises a differential pressure sensor that directly measures the ratio or difference between a pressure upstream of said restriction and a pressure downstream of said restriction.

9. The method of claim 6, wherein said differential pressure sensor comprises a first absolute pressure sensor positioned to measure a pressure upstream of said restriction and a second absolute pressure sensor positioned to measure a pressure downstream of said restriction.

10. The method of claim 6, wherein said particle impactor system further comprises a second pressure sensor for measuring said ambient pressure inside or outside said system.

11. The method of claim 10, wherein said particle impactor system further comprises a third pressure sensor, wherein said second pressure sensor measures an ambient pressure outside of said system and said third pressure sensor measures a pressure inside said system.

12. The method of claim 3, wherein said particle impactor system further comprises a mass flow sensor for determining said flow rate of said fluid, wherein said mass flow sensor is positioned in fluid communication with said plurality of intake apertures, said fluid outlet or both said plurality of intake apertures and said fluid outlet.

13. The method of claim 1, wherein said step of determining said ambient pressure comprises determining an absolute pressure outside said particle impactor system, determining an absolute pressure within said particle impactor system, or determining both an absolute pressure outside said particle impactor system an absolute pressure within said particle impactor system.

14. The method of claim 1, wherein the method uses only two pressure sensors.

15. The method of claim 1, wherein said step of determining said volumetric flow rate comprises determining said volumetric flow rate as Q in the following relationship (FX1):

$$Q = k \cdot [(2 \cdot P_{DPS})/P_{APSE}]^{1/2} \quad \text{(FX1)};$$

(FX1) where k is an empirically determined constant, PDPS is a differential pressure within the system and PAPSE is said ambient pressure.

16. The method of claim 15, wherein said differential pressure (PDPS) is across a restriction within said particle impactor system.

17. The method of claim 1, wherein said step of determining said volumetric flow rate comprises determining said volumetric flow rate as Q in the following relationship (FX2):

$$Q = k \cdot [(P_{APSO} \cdot P_{DPS})]^{1/2}/P_{APSE} \quad \text{(FX2)};$$

where k is an empirically determined constant, PAPSO is an absolute pressure within said particle impactor, PDPS is a differential pressure within the system and PAPSE is said ambient pressure.

18. The method of claim 1, wherein said step of determining said volumetric flow rate comprises utilizing the following relationship (FX3) in evaluation of Q:

$$Q = k \cdot [(2\Delta P)/\rho]^{1/2} \quad \text{(FX3)};$$

where k is an empirically determined constant; where $\Delta P$ is a differential pressure across a restriction in said particle impactor system and p is a density of said fluid.

19. The method of claim 1, wherein said step of determining said flow rate of said fluid comprises determining a mass flow rate of said fluid.

20. The method of claim 1, further comprising a step of:
increasing an absolute pressure within the particle impactor system if the volumetric flow rate is determined to be larger than a specified value; or
reducing an absolute pressure within the particle impactor system if the volumetric flow rate is determined to be smaller than a specified value.

21. The method of claim 1, wherein said fluid flow is generated by one or more flow generating devices selected from the group consisting of a fan, a blower, a pump and any combination of these.

22. The method of claim 21, further comprising a step of:
reducing a speed of one or more of said flow generating devices if said volumetric flow rate is determined to be larger than a first specified value; or
increasing a speed of one or more of said flow generating devices if said volumetric flow rate is determined to be smaller than a second specified value.

23. The method of claim 1, wherein said fluid comprises air or one or more process gases.

24. The method of claim 1, wherein the impact surface comprises a receiving surface of a growth medium.

25. A method of measuring a volumetric flow rate of a fluid flow through a particle impactor system, the method comprising the steps of:
pulling said fluid through a plurality of intake apertures of a sampling head of said particle impactor system, wherein said fluid contains a plurality of particles;
pulling said fluid past an impact surface positioned in fluid communication with each of said plurality of intake apertures, causing a change in direction of said fluid, whereby at least a portion of the particles are directed onto said impact surface for collection;
determining a flow rate of said fluid;
determining ambient pressure; and
determining said volumetric flow rate as a function of said flow rate of said fluid and said ambient pressure.

26. The method of claim 25, wherein the impact surface comprises a receiving surface of a growth medium.

27. A particle impactor system comprising:
a sampling head having a plurality of intake apertures;
an impact surface positioned in fluid communication with each of said plurality of intake apertures;
an impactor base supporting said impact surface, wherein said impactor base comprises a fluid outlet, wherein said sampling head and said impactor base together form a fluid tight seal such that fluid can only flow into or out of said particle impactor system through said plurality of intake apertures and said fluid outlet;
a flow restriction positioned in fluid communication with said plurality of intake apertures, said fluid outlet or both said plurality of intake apertures and said fluid outlet;
first pressure sensor comprising a differential pressure sensor positioned to measure a differential pressure across said restriction; and
a second pressure sensor positioned to measure an ambient pressure inside or outside of said system.

28. The system of claim 27, wherein said first pressure sensor comprises a differential pressure sensor capable of directly measuring said differential pressure.

29. The system of claim 27, wherein said differential pressure sensor comprises a first absolute pressure sensor positioned to measure a pressure upstream of said restriction and a second absolute pressure sensor positioned to pressure downstream of said restriction.

30. The system of claim 27, wherein said particle impactor system further comprises a third pressure sensor, wherein said second pressure sensor measures an ambient pressure outside of said system and said third pressure sensor measures an ambient pressure inside said system.

31. The system of claim 27 further comprising a mass flow sensor positioned in fluid communication with said plurality of intake apertures, said fluid outlet or both said plurality of intake apertures and said fluid outlet.

32. The system of claim 27, further comprising a processor positioned in data communication with said first and second pressure sensors, said processor programmed with instructions that when executed determine a volumetric flow rate using pressure measurements from said first and second pressure sensors.

33. The system of claim 32, wherein said processor is programmed with instructions that when executed determine the volumetric flow rate as Q according to the following relationship (FX1):

$$Q = k \cdot [(2 \cdot P_{DPS})/P_{APSE}]^{1/2} \quad \text{(FX1)};$$

where k is an empirically determined constant, PDPS is a differential pressure in the system and PAPSE is said ambient pressure.

34. The system of claim 32, wherein said processor is programmed with instructions that when executed determine the volumetric flow rate as Q according to the following relationship (FX2):

$$Q = k \cdot [(P_{APSO} \cdot P_{DPS})]^{1/2}/P_{APSE} \quad \text{(FX2)};$$

where k is an empirically determined constant, PAPSO is an absolute pressure within said system, PDPS is a differential pressure in the system and PAPSE is said ambient pressure.

35. The system of claim 32, wherein said processor is programmed with instructions that when executed determine the volumetric flow rate as Q according to the following relationship (FX3):

$$Q = k \cdot [(2\Delta P)/\rho]^{1/2} \quad \text{(FX3)};$$

where k is an empirically determined constant, where $\Delta P$ is a differential pressure across said restriction and p is a density of a fluid flowing through said restriction.

36. The system of claim 32, wherein said processor is further positioned in data communication with a flow controller and wherein said processor is programmed with instructions that when executed adjust a flow set point of said flow controller.

37. The system of claim 36, wherein said flow controller is positioned to control a fluid flow rate of one or more flow generating devices positioned in fluid communication with said plurality of intake apertures, said fluid outlet or both said plurality of intake apertures and said fluid outlet, wherein said one or more flow generating devices are selected from the group consisting of a fan, a blower, a pump and any combination of these.

38. The system of claim 27, further comprising one or more flow generating devices selected from the group consisting of a fan, a blower, a pump and any combination of these, wherein said one or more flow generating device are positioned in fluid communication with said plurality of intake apertures, said fluid outlet or both said plurality of intake apertures and said fluid outlet.

39. The system of claim 27, wherein the impact surface comprises a receiving surface of a growth medium.

* * * * *